(12) United States Patent
Jain et al.

(10) Patent No.: US 9,757,417 B2
(45) Date of Patent: Sep. 12, 2017

(54) BIOACTIVE GLASS PREPARATION AND USE

(71) Applicant: Lehigh University, Bethlehem, PA (US)

(72) Inventors: Himanshu Jain, Bethlehem, PA (US); Roman Holovchak, Clarksville, TN (US); Matthias M. Falk, Emmaus, PA (US)

(73) Assignee: Lehigh Universtiy, Bethlehem, PA (US)

( * ) Notice: Subject to any disclaimer, the term of this patent is extended or adjusted under 35 U.S.C. 154(b) by 0 days.

(21) Appl. No.: 15/297,680

(22) Filed: Oct. 19, 2016

(65) Prior Publication Data

US 2017/0035805 A1 Feb. 9, 2017

Related U.S. Application Data

(63) Continuation of application No. 14/526,319, filed on Oct. 28, 2014, now abandoned.

(60) Provisional application No. 61/896,227, filed on Oct. 28, 2013.

(51) Int. Cl.

| | |
|---|---|
| *A61K 33/42* | (2006.01) |
| *C03C 3/097* | (2006.01) |
| *C03C 4/00* | (2006.01) |
| *C03B 32/02* | (2006.01) |
| *C03B 19/02* | (2006.01) |
| *A61K 33/00* | (2006.01) |
| *A61K 33/08* | (2006.01) |
| *A61L 27/10* | (2006.01) |
| *A61L 27/54* | (2006.01) |

(52) U.S. Cl.
CPC .............. *A61K 33/42* (2013.01); *A61K 33/00* (2013.01); *A61K 33/08* (2013.01); *A61L 27/10* (2013.01); *A61L 27/54* (2013.01); *C03B 19/02* (2013.01); *C03B 32/02* (2013.01); *C03C 3/097* (2013.01); *C03C 4/0007* (2013.01); *C03C 4/0014* (2013.01); *A61L 2430/34* (2013.01); *C03C 2204/00* (2013.01)

(58) Field of Classification Search
None
See application file for complete search history.

(56) References Cited

U.S. PATENT DOCUMENTS

| | | | | |
|---|---|---|---|---|
| 5,686,091 | A | * 11/1997 | Leong | A61F 2/022 264/41 |
| 8,389,018 | B2 | 3/2013 | Jain | |
| 2010/0015244 | A1* | 1/2010 | Jain | A61L 27/56 424/602 |

OTHER PUBLICATIONS

Fischer, R.X. et al., "Short Communication—Revised data for combeite, Na Ca2Si3O9," Acta Crystallographica, Section C 43, (1987), pp. 1852-1854.
Golovchak et al., "Influence of phase separation on the devitrification of 45S5 bioglass," Acta Biomater (2014), pp. 1-9.
Malek, J., "Kinetic analysis of crystallization processes in amorphous materials," Thermochimica Acta, vol. 355, Issue 1-2 (2000), pp. 239-253.
Ohsato, H. et al., "Structure of Na2 CaSi2O6," Acta Crystallographica, Section C 41, (1985), pp. 1575-1577.
Sola, A. et al., "Heat Treatment of Na2O—CaO—P2O5—SiO2 bioactive glasses: Densification processes and postsintering bioactivity," J. Biomater. Res. Part A 100A: 305-322 (published online Nov. 2, 2011).

* cited by examiner

*Primary Examiner* — David J Blanchard
*Assistant Examiner* — Daniel F Coughlin
(74) *Attorney, Agent, or Firm* — Saul Ewing LLP

(57) ABSTRACT

A process of preparing a glass comprising: (a) heating a mixture of precursor chemicals to a melt temperature to form a melt, the melt being characterized in that quenching the melt at or above a threshold temperature results in a spinodal phase separation, and quenching the melt below the threshold temperature results in a droplet phase separation; and (b) quenching the melt at or above the threshold temperature in a preheated mold to form the glass composition having the spinodal phase separation.

6 Claims, 18 Drawing Sheets

Fig. 14(i)                    Fig. 14(ii)
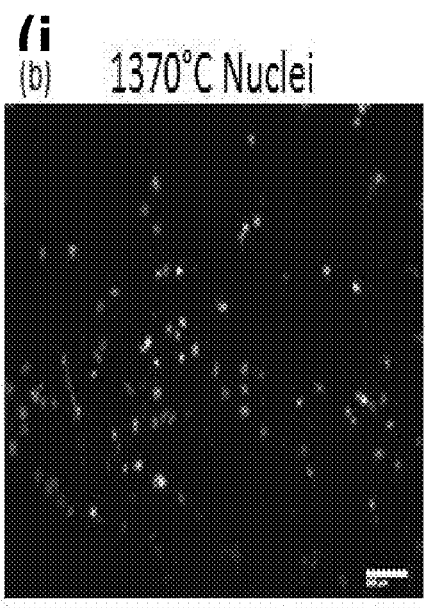
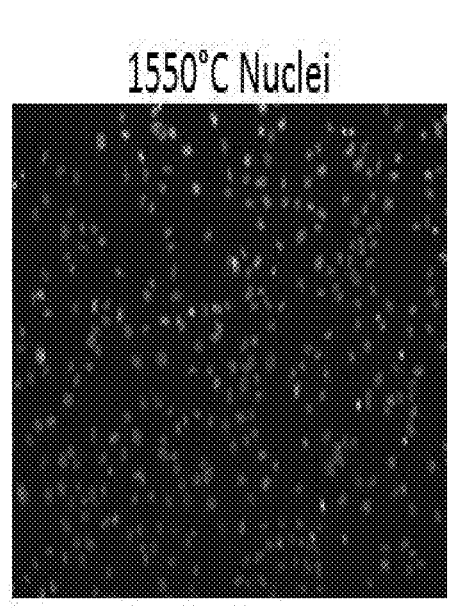
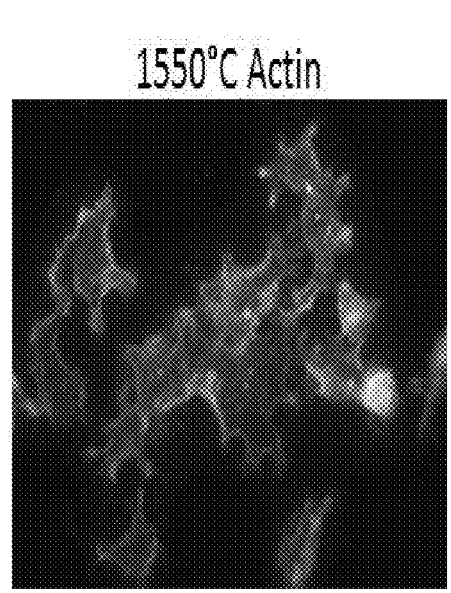
Fig. 14 (iii)                 Fig. 14(iv)

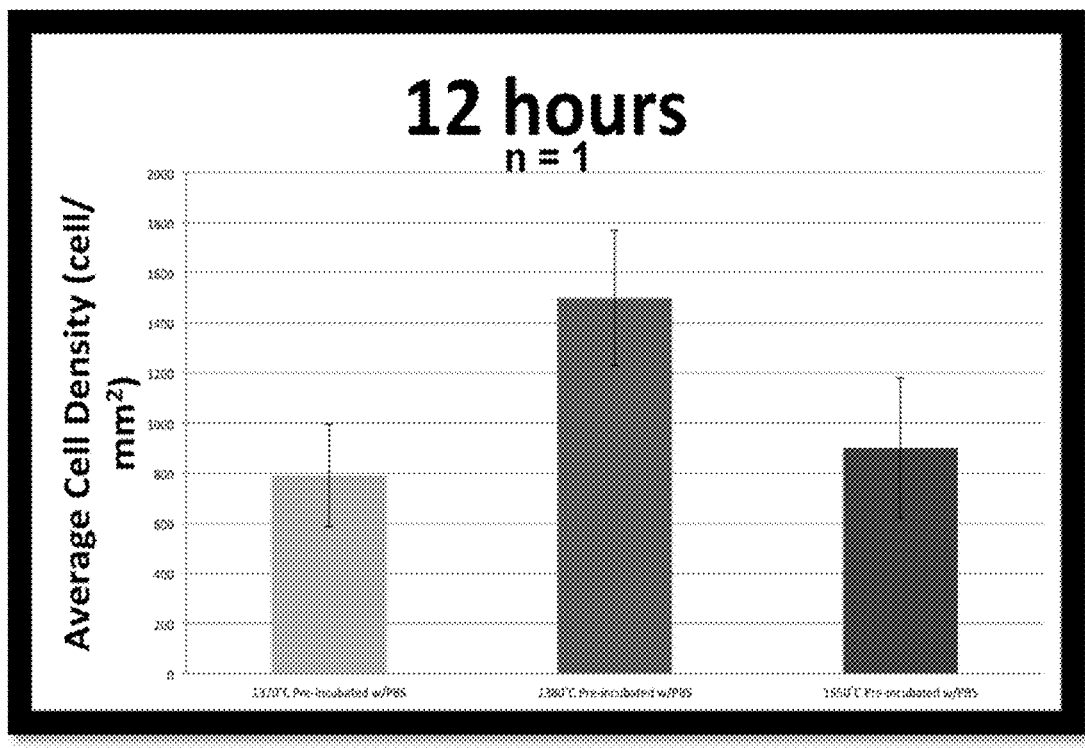
Fig. 15(iii)

BIOACTIVE GLASS PREPARATION AND USE

REFERENCE TO RELATED APPLICATION

This application is a continuation of U.S. application Ser. No. 14/526,319, filed on Oct. 28, 2014, which claims the benefit under 35 U.S.C. §119(e) of U.S. Provisional Application No. 61/896,227, filed on Oct. 28, 2013 each of which is incorporated by reference in its entirety.

STATEMENT OF GOVERNMENT INTEREST

This invention was made with government support under the National Science Foundation, grant number DMR-0602975 and the International Materials Institute for New Functionality in Glass, grant number DMR-0844014. The government has certain rights in the invention.

FIELD OF INVENTION

The present invention relates generally to a bioactive glass and, more specifically, to a bioactive glass prepared to favor spinodal phase separation.

BACKGROUND

With the advent of tissue engineering, the scientific and medical communities are rapidly shifting from an emphasis on tissue replacement to tissue regeneration. Bioactive glass has been recognized for its remarkable biocompatibility and its potential has recently been growing as a highly promising material for hard tissue repair and regeneration.

Manufacturing methods and post-fabrication treatment of 45S5 glass ($45SiO_2$-$24.5Na_2O$-$24.5CaO$-$6P_2O_5$ by wt. %), which is a well-known bioglass, are shown to have a significant impact on its biological response. Many studies have been devoted to understand the effect of devitrification of this bioactive glass (BG) on its physical properties as well as biological performance such as its ability to promote bone growth and regeneration. The BG-derived glass-ceramics (crystalline or semi-crystalline) or bioscaffolds prepared by the sintering of their powder exhibit suitable mechanical properties along with broader engineering possibilities. At the same time, the glass-ceramics, compared to BG, show different solubility in body fluid and possibly the protein adsorption profile (protein amount and conformation can depend on surface morphology)—a key factor influencing cells attachment. A common argument is that the phosphorous distribution changes upon crystallization of a glass, causing phosphorous dissolution profile to change, which ultimately affects the distribution of binding sites for proteins and the time to form the hydroxycarbonate apatite (HCA) layer needed for tissue integration.

Although the phosphorous dissolution profile may affect bioactivity, Applicants, recognize that nanostructure of the glass also plays a significant role in promoting bioactivity, and have identified a need to investigate and establish the desirable nanostructure of glass and its effects on bioactivity. The present invention fulfills this need among others.

SUMMARY OF INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

Despite the progress in the applications of 45S5 BG and corresponding ceramics, the fact that this composition belongs to the immiscibility domain of corresponding phase diagram appears to be largely unappreciated. The origin of such phase separation pertains to a positive enthalpy of mixing, which drives a glass-forming liquid to separate spontaneously into two compositionally distinct phases. It is a process concurrent to the maximization of entropy, which usually results in a homogeneous mixing of the constituents in glass. Liquid-liquid immiscibility can lead to droplet-like or spinodal-type phase separation in the glassy state. Droplet phase separation is characterized by a sharp boundary between the composition of droplets and rest of the matrix, while in spinodal decomposition, the phase separated system consists of two interpenetrating networks of diffuse compositional boundary between the two immiscible phases. In the latter case, the compositions of two phases evolve simultaneously as the degree of phase separation increases and the boundary between phases becomes more distinct.

One aspect of the present invention is Applicants' recognition that 45S5 glass/ceramic product can be phase-separated at the nanoscale, and can have unique properties depending on the quenching rate or post-fabrication treatment (annealing, etc.). Specifically, different degrees of spinodal phase separation with two interpenetrating phases can be obtained by varying the melt temperature within 1400-1600° C. range and casting into preheated molds. Additionally, Applicants discovered that glass compositions have a threshold temperature for quenching, above which results in glass with a spinodal phase separation, and below which results in the glass with a droplet phase separation. For example, quenching a meld of 45S5 at 1380° C. tends to produce spinodal phase separation, while quenching at 1370° C. tends to produce droplet phase separation. Thus, for 45S5, the threshold temperature lies between 1370 and 1380° C.

On the other hand, conventional glass is manufactured to produce homogeneous, defect free solid at the lowest cost, which implies working at the lowest possible temperature and using minimum number of processing steps. For example, the conventional 45S5 glass may be melted at temperatures below 1400° C., cast in a mold at ambient temperature and then annealed to relieve stresses. Applicants recognize that in this conventional process, the nucleation and growth mechanism, which produces isolated droplets in an otherwise continuous phase, overrules spinodal type phase separation when melt is cast from 1250-1400° C. into unheated molds. In contrast, the glass produced from the method of the present invention has interconnected phases in a spinodal type microstructure (unlike commonly prepared glass of same composition), which may be single phase or have phase separation as droplets in a continuous matrix. Thus, the nanostructure of 45S or any other glass, can be controlled by varying the temperature at which the melt is maintained before casting, the temperature of the mold and subsequent cooling routine.

Another aspect of the present invention is the examination of the classic melt-quenched 45S5 glass composition with signatures of droplet-like or spinodal phase-separation at the nanoscale, as well as corresponding ceramics prepared by the devitrification of these parent glasses. In this respect, little is known about the influence of nanoscale phase-separation on the performance of scaffolds made of 45S5 BG and/or corresponding glass-ceramics. For instance, the physical properties of 45S5 glass phase-separated at the nanoscale, and the influence of this phase separation on the crystallization kinetics, glass-ceramics formation, HCA layer formation, or ionic dissolution/leaching rates is generally unexplored.

Applicants discovered that the type of phase separation (such as spinodal vs. droplet-like) has a pronounced effect on a variety of characteristics, including the activation energy of viscous flow and crystallization, the onset temperature of crystallization, and the void size distribution at the nanoscale. Furthermore, Applicants examined the cellular ability to detect differences in nanostructure on 45S5 bioactive glass samples. Applicants have discovered that a 45S glass comprising spinodal type nanostructure is biomedically superior to the 45S glass comprising droplet type nanostructure. Specifically, Applicants found cells showed a preference to the spinodal phase separation as opposed to the droplette distribution, suggesting that cells are somehow sensing the details of the morphology of the substrates that are about 1000 times smaller than the cells themselves. The advantage of spinodal nanostructure applies not only to 45S5, but also to other silicate compositions as well, such as those derived from standard 45S composition for instance.

Therefore, Applicants not only realized the importance of the spinodal and droplette nanostructure of glass and identified a method of producing each, but also recognized that phase separation nanostructure has significant effects on the characteristics of the glass, including the ability of cells to attach and proliferate on the glass material.

One aspect of the invention is a method of preparing a glass composition by quenching a glass melt at or above a threshold temperature to promote a spinodal phase separation. In one embodiment, the method comprises: (a) heating a mixture of chemicals to a melt temperature to form a melt, the melt being characterized in that quenching the melt at or above a threshold temperature results in a spinodal phase separation, and quenching the melt below the threshold temperature results in a droplet phase separation; and (b) quenching the melt at or above the threshold temperature in a preheated mold to form the glass composition having the spinodal phase separation.

Another aspect of the invention is a glass composition prepared by quenching a glass melt at or above a threshold temperature to promote a spinodal phase separation. In one embodiment, the glass composition is prepared by the process comprising: (a) heating a mixture of chemicals to a melt temperature to form a melt, the melt being characterized in that quenching the melt at or above a threshold temperature results in a spinodal phase separation, and quenching the melt below the threshold temperature results in a droplet phase separation; and (b) quenching the melt at or above the threshold temperature in a preheated mold to form the glass composition having the spinodal phase separation.

Yet another aspect of the invention is a method of using the glass composition to promote cellular attachment and proliferation. In one embodiment, the method comprises: (a) disposing the glass composition in a cellular environment, the glass being prepared by a process comprising at least: (i) heating a mixture of chemicals to a melt temperature to form a melt, the melt being characterized in that quenching the melt at or above a threshold temperature results in a spinodal phase separation, and quenching the melt below the threshold temperature results in a droplet phase separation; and (ii) quenching the melt at or above the threshold temperature in a preheated mold to form the glass composition having the spinodal phase separation; and (c) facilitating cellular attachment and proliferation on the glass composition.

BRIEF DESCRIPTION OF FIGURES

FIGS. 14(i)-(iv) illustrate nanostructure affecting cellular density and adhesion.

DETAILED DESCRIPTION

Figures 1A, 1B, 1C:
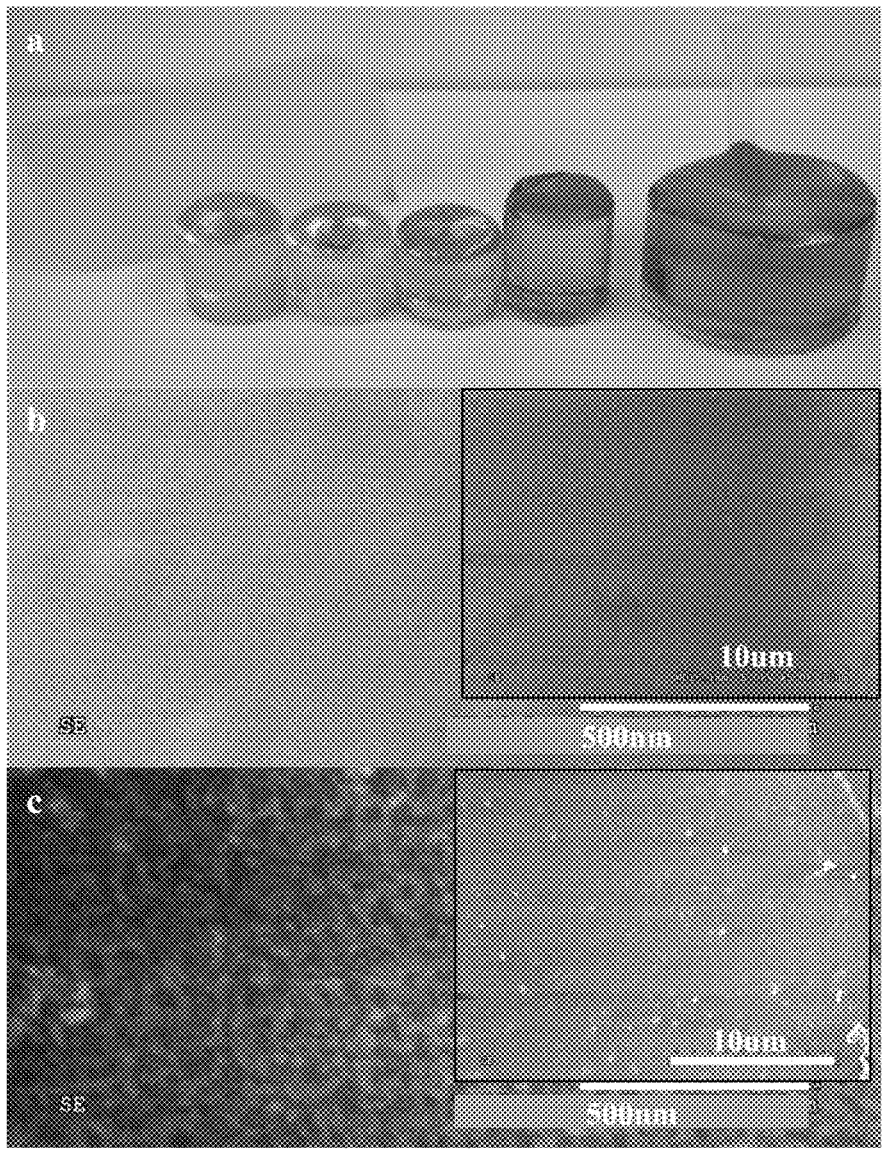
FIG. 1(a) shows 45S5 glasses phase separated to different degrees.
FIGS. 1(b) and (c) show SEMs of droplet-like phase separation and spinodal phase separation, respectively.

In one embodiment, the present invention involves a process of preparing a glass comprising heating a mixture of chemicals to a melt temperature to form a melt, the melt being characterized in that quenching the melt at or above a threshold temperature results in a spinodal phase separation, and quenching the melt below the threshold temperature results in a droplet phase separation; and quenching the melt at or above the threshold temperature to form the glass composition having the spinodal phase separation.

The mixture may be any mixture for producing a glass having spinodal phase separation. Suitable mixtures include, for example, the mixture of high purity (99.99% or better) $CaCO_3$, $Na_2CO_3$, silicon dioxide $SiO_2$ and calcium phosphate tribasic $Ca_5OH(PO_4)_3$ powders, for 45S5 glass (45 wt.

% $SiO_2$-24.5 wt. % $Na_2O$-24.5 wt. % CaO-6 wt. % $P_2O_5$), and other bioactive silicate glasses that are prone to phase separation, for example, the derivatives of 45S5 composition doped with the oxides of silver, zinc, strontium, boron, titanium, etc., or different ratios of the constituents of 45S5 composition.

The melt temperature can vary based on the mixture and other process parameters including the temperature of the mold and quenching temperature. For example, suitable results have been obtained for 45S5 having a melt temperature of about 1400 to about 1600° C. As mentioned above, this melt temperature is generally higher than that used to prepare conventional 45S5. Applicants recognize that in the conventional process, the nucleation and growth mechanism, which produces isolated droplets in an otherwise continuous phase, overrules spinodal type phase separation when the melt is cast, for example, from 1250-1400° C. into unheated molds. In contrast, the glass produced from the method of the present invention has interconnected phases in a spinodal type distribution. A different degree of spinodal phase separation with two interpenetrating phases can be obtained by varying the melt temperature within 1400-1550° C. range and casting into preheated molds. In one embodiment, the melt temperature is about 1450 to about 1550° C., and, in a more particular embodiment, the melt temperature is about 1550° C.

The threshold temperature will vary depending on the composition of the mixture, among other variables. For example, suitable results have been obtained in which the threshold temperature is no less than about 86% of the melt temperature. In a more particular embodiment, the threshold temperature is no less than about 88.5% of the melt temperature, and in a more particular embodiment, the threshold temperature is no less than about 89% of the melt temperature. For example, in one embodiment, in which the molds are heated above 100° C. and a 45S5 mixture is used, the threshold temperature is no less than about 1375° C. In a more particular embodiment, the threshold temperature ranges from 1375 to about 1550° C., and in a still more particular embodiment, the threshold temperature ranges from about 1375 to about 1380° C.

In one embodiment, the quenching comprises pouring the melt into a preheated mold. Again, the degree to which the mold is preheated will depend on the mixture and other heating parameters, although suitable results have been achieved with a mold preheated above 100° C. In a more particular embodiment, the mold is preheated to about 100 to about 300° C.

It should be understood that the process of the preparing the spinodal phase separated glass may involve other steps which are well known in the art. For example, in one embodiment, the mixture is calcined before forming the melt. Suitable results have been achieved when calcining at about 800° C. for 4-7 hours.

Additionally, it may be preferable to cool the melt from its melt temperature prior to quenching. For example, in one embodiment, the melt is allowed to cool gradually from 1550° C. before being quenched. In one particular embodiment, the melt is allowed to cool to 1380° C. before it reaches the threshold temperature.

Another aspect of the invention is the product made from the process described above.

Still another aspect of the invention is a method of using the glass composition to promote cellular attachment and proliferation. As mentioned above, an aspect of the invention is the recognition and discovery that the nanoscale structure of glass is important for its biomedical performance. In particular, Applicants have found that the in vitro performance of glass is superior when its structure comprises of interconnected spinodally phase separated nanostructure as opposed to the same glass with isolated droplets in a matrix. Cells respond more favorably to the morphology and composition of the phases in the former structure than in the latter structure. Applicants note that, within the broad classification of spinodal or droplet type nanostructures, significant variations of the distribution of two phases may also impact the cell response. In other words, the conditions of glass fabrication may be further optimized for improving the cell response, but the basic premise of superior performance of the spinodal nanostructure will remain. This advantage of spinodal nanostructure applies to other silicate compositions as well, such as those derived from standard 45S5 composition for instance.

In one embodiment, the method comprises disposing the glass composition made from the process described above in a cellular environment, and then facilitating cellular attachment and proliferation on the glass composition. The cellular environment may be any fluid environment having living cells. Such an environment may be, for example, in a Petri dish or in an animal body. Facilitating attachment and proliferation means broadly maintaining the environment to enable the cells to live for a significant period. Such cellular environments and conditions for maintaining them are well known in the art.

EXAMPLE 1

The following example demonstrates the different phase separations that can be formed depending on whether the melt is quenched at or above the threshold temperature, or below the threshold temperature. Further, these examples illustrate the different properties and influences the different phase separations have. Note these results are published in Golovchak et al. *Influence of phase separation on the devitrification of 45S5 bioglass*, Acta Biomater (2014), http://dx.doi.org/10.1016/j.actbio.2014.07.024 hereby incorporated by reference. Note that these are just examples, and that, one may find other combination of process parameters to obtain the two types of nanostructures.

Figure 11:
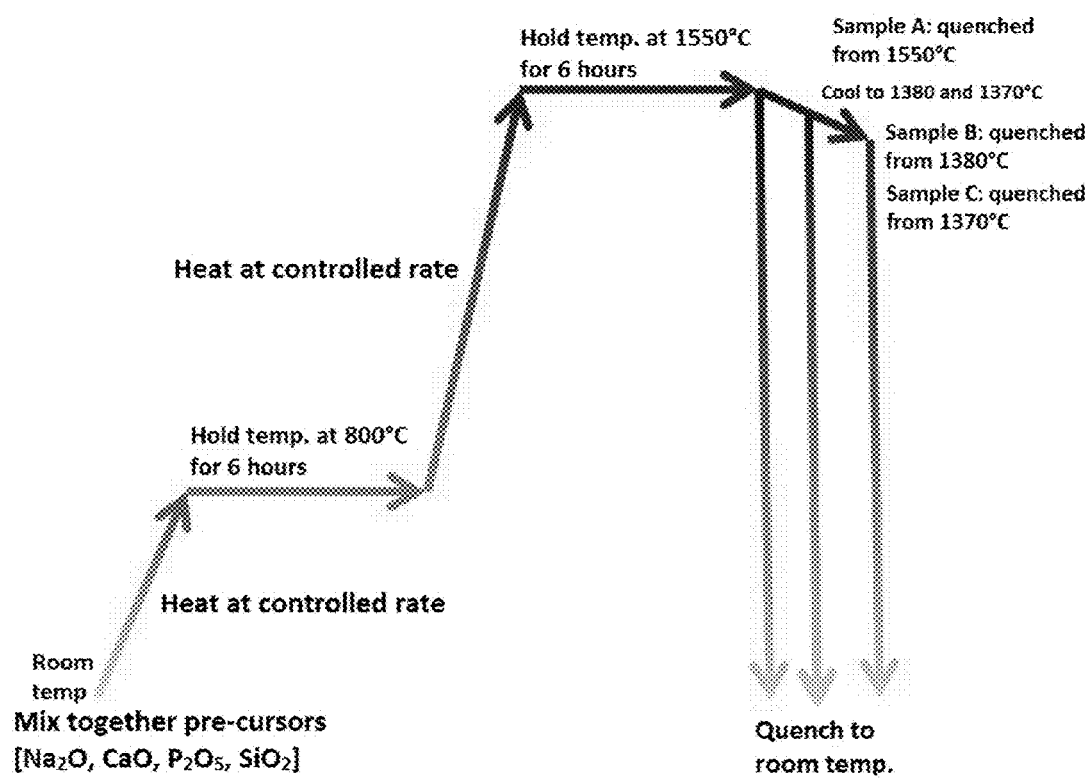
FIG. 11 is a schematic of one embodiment of the method of the present invention.

Referring to FIG. 11, a schematic of one embodiment of the method of preparing the glass composition of the present invention is shown. Specifically, a 45S5 glass ($45SiO_2$-$24.5Na_2O$-$24.5CaO$-$6P_2O_5$ by wt. %) was synthesized using melt-quenching and casting in stainless steel molds. High purity (99.99% or better) carbonates $CaCO_3$, $Na_2CO_3$, silicon dioxide $SiO_2$ and calcium phosphate tribasic $Ca_5OH$ $(PO_4)_3$ powders were used as raw precursors, and melted in a Pt crucible. The powder of a given sample was obtained by ball milling (~1 hour) of bulk pieces followed by sieving through a collection of 5 sieves (500 μm, 300 μm, 150 μm, 75 μm, 32 μm) to separate particles by size.

The mixture of starting precursor powders was calcined at 800° C. for 6 hours and then slowly (2 K/min) heated till the maximum melt temperature of 1550° C., where it was maintained at least 3 hours to homogenize the melt. To induce spinodal phase decomposition the melt was quenched from 1550° C. into preheated (200-400° C.) molds. Different degrees of spinodal phase separation with two interpenetrating phases are obtainable by varying the melt temperature within 1400-1550° C. range and casting into preheated molds. The nucleation and growth mechanism, which produces isolated droplets in an otherwise continuous phase, overrules spinodal type phase separation when melt is cast from 1250-1400° C. into unheated molds. Thus the nanostructure of 45S glass, which can be controlled by varying the temperature at which the melt is maintained before casting, the temperature of the mold and subsequent cooling routine.

For comparison a commercial 45S5 Bioglass was used, which had pronounced droplet-like phase separation. The two types of phase-separation (i.e., spinodal and drop-like) arise from the difference in the melt temperature just prior to casting, and the quench rate during solidification.

The 45S5 glasses were transformed into glass-ceramics by heating in two steps—annealing of the material at 650-670 C for 3 hours to induce crystal nucleation, followed by another heat treatment at ~730-750° C. for 6 hours to facilitate their growth.

The average composition of the prepared glasses was checked with X-ray photoelectron spectroscopy (XPS). No significant difference was found between the droplet-like and spinodally phase separated glasses as set forth in Table 1.

TABLE 1

Composition of the investigated spinodally and droplet-like phase separated 45S5 glasses and derived ceramics. determined from XPS data.

| Sample | Composition, at. % | | | | |
|---|---|---|---|---|---|
| | O | Si | Ca | Na | P |
| Theoretical | 55.2 | 16.3 | 9.5 | 17.2 | 1.8 |
| Spinodally phase-separated glass | 50.1 | 18.9 | 8.8 | 20.5 | 1.6 |
| Ceramics out of spinodally phase-separated glass | 49.4 | 19.3 | 9.4 | 19.9 | 1.9 |
| Droplet-like phase-separated glass | 49.8 | 17.9 | 9.0 | 21.3 | 1.9 |
| Ceramics out of droplet-like phase-separated glass | 50.7 | 19.0 | 8.8 | 19.4 | 2.3 |

The XPS spectra were recorded in a normal emission mode on sample surfaces freshly fractured inside the ultrahigh vacuum of the Scienta ESCA-300 spectrometer using monochromatic Al Kα X-rays (1486.6 eV). The XPS data consisted of survey scans over the entire binding energy (BE) range and selected scans over the core-level photoelectron peaks of interest. The surface charging from photoelectron emission was neutralized using a low energy (<10 eV) electron flood gun. The experimental positions of core levels for all of the investigated samples were adjusted by referencing to the 1 s core level peak of adventitious carbon at 284.6 eV. Data analysis of the XPS spectra was conducted using the standard CASA-XPS software package.

Positron annihilation lifetime (PAL) spectra were recorded with the fast coincidence system of 230 ps resolution (FWHM of a single Gaussian, determined by measuring 60Co isotope) at the temperature, T=22° C. and relative humidity, RH=35%. Each PAL spectrum was measured with a channel width of 6.15 ps (total number of channels 8000) and contained $3 \cdot 10^6$ coincidences in total. Isotope $^{22}$Na (activity ~50 kBq) was used as source of positrons (prepared from aqueous solution of $^{22}$NaCl, wrapped with Kapton® foil of 12 μm thickness and sealed), which was sandwiched between two identical samples. All the PAL spectra of the investigated samples (dried at 120° C. for 4 hours in vacuum before the measurements) were decomposed into four discrete exponentials $s(t)=\Sigma(I_i/\tau_i)\exp(-t/\tau_i)$ with average positron lifetime $\tau_i$ and intensity $I_i$ of $i^{th}$ positron decay component (i=1 to 4) using standard LT 9.0 program. The additional peaks into the envelope of fitted curve were added only if they significantly improved goodness of the fit. The uncertainties in the determination of lifetimes ($\tau_i$) and corresponding intensities ($I_i$) were ±0.005-0.5 ns (increasing with increasing $\tau_i$) and ±0.2-1%, respectively.

FT-IR measurements on samples polished to high optical quality were performed in a reflection mode (nearly normal incident angle), using Varian 7000e spectrometer.

Rigaku "MiniFlex II" diffractometer was used for X-ray powder diffraction (XRD) studies. The XRD patterns were recorded within 15-60° angular range, 0.02° scan step and 1 s integration time.

DSC data were acquired for bulk and powder samples using NETZSCH 404/3F microcalorimeter pre-calibrated with a set of standard elements. DSC curves were recorded in a nitrogen atmosphere with 2, 5, 10, 15 and 20 K/min heating rates. Three independent DSC measurements were performed in each case to confirm the reproducibility of the obtained results. Raw DSC data were processed using NETZSCH PC software package.

Spinodally phase-separated 45S5 glass appears slightly purple in the reflected light in comparison to the glass with droplet-like phase separation (FIG. 1a). This color originates from the scattering of light caused by the co-existence of two interconnected phases with close refractive indexes; UV-VIS spectroscopy testified that no characteristic color lines were present in UV-VIS absorption spectra. High-resolution SEM images in FIG. 1b,c show the difference in the structure of the colorless and purple tinged glasses at the nanoscale. Two interconnected phases can be clearly seen in FIG. 1c, which is characteristic of spinodal type phase decomposition, whereas fingerprints of droplet-like phase separation with sharp compositional boundaries are visible on the surface of colorless samples (FIG. 1b). In the latter case, the droplets are too big (~1 μm) to cause color as a result of scattering. However, in both cases the matrix of the investigated glasses consists of two immiscible amorphous phases: one is supposed to be silica-rich and the other containing more sodium/calcium ions and phosphorus.

Figure 2:
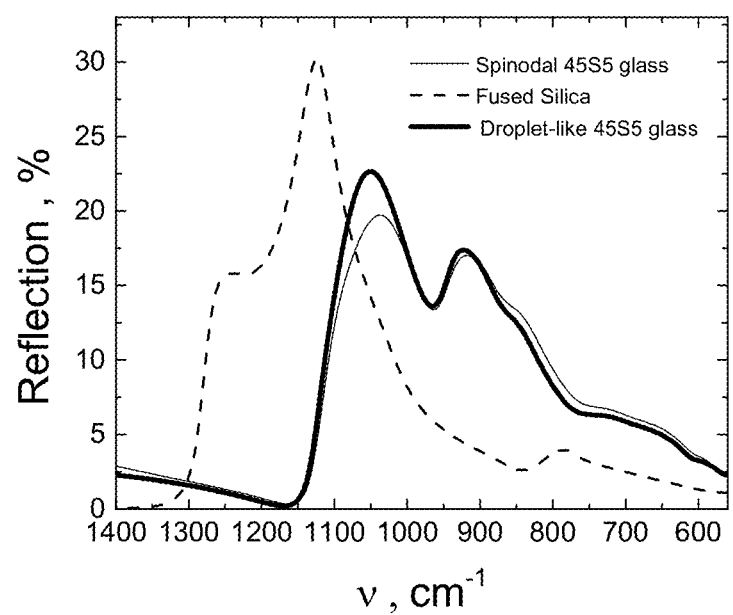
FIG. 2 shows FT-IR spectra of droplet-like and spinodally phase separated 45S5 glasses, with spectrum of fused silica shown for comparison.

FT-IR reflection spectra of the two types of 45S5 glasses recorded in the region of fundamental vibrations absorption show only subtle differences (FIG. 2), which is not surprising owing to the integral nature of the measured spectra (averaged through a relatively large macroscopic surface area). As compared to fused silica, where the bending vibrations of $SiO_4$ tetrahedral units at ~800 $cm^{-1}$, asymmetric stretch modes at ~1123 $cm^{-1}$ and ~1220 $cm^{-1}$ are observed (FIG. 2), the 45S5 glass has these optical modes shifted towards lower frequencies (~700 $cm^{-1}$ for bending and ~1050-1100 $cm^{-1}$ for asymmetric stretching vibrations, respectively), which is typical for any other alkali and alkaline earth containing glasses. Also, new bands at ~900 and ~850 $cm^{-1}$ emerge, which are associated with the stretching vibrations of $SiO_4$ tetrahedra having one or two non-bridging oxygens (NBO) in the nearest surrounding of Si atoms (so-called $Q^3$ and $Q^2$ groups). The band at ~600 $cm^{-1}$ is usually attributed to phosphate complexes, having P—O bending vibrations in this range.

In principle, viscosity of the phase separated silicate glass should be higher than the viscosity of homogeneous glass of the same composition, because the separated silica-rich matrix has high viscosity and dominates flow behavior. Indeed, the activation energy of viscous flow for the phase separated glasses, calculated using Ozawa plot for glass transition temperature determined at various heating rates, is found to be dependent on the degree and type of phase separation. Thus, the value of the activation energy of viscous flow for spinodally phase separated glass was found to be ~100 kJ/mol lower than the one for droplet-like phase separated 45S5 glass. We can speculate then that in the case of droplet-like phase separation more alkaline ions are removed from the glass matrix into the droplets, leading to higher viscosity of the residual silica-rich phase.

Figure 3A:
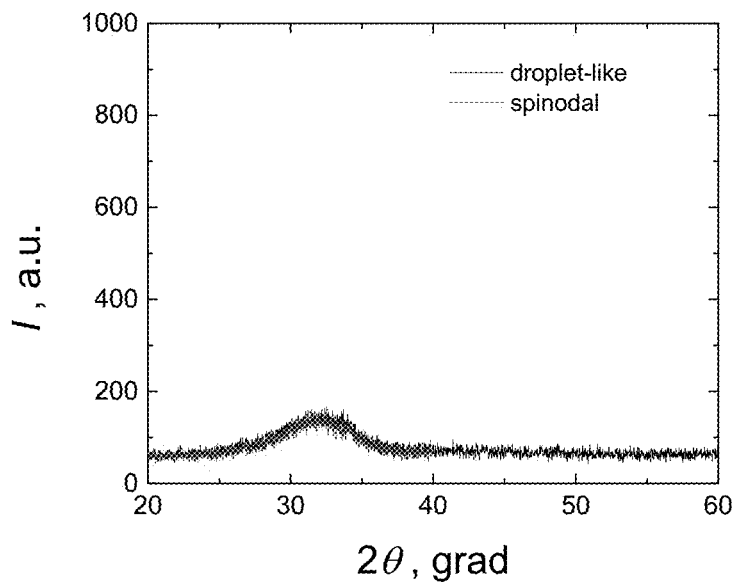
FIGS. 3(a) and (b) show XRD spectra of spinodally and droplet-like phase separated 45S5 glasses, and obtained ceramics, respectively.
Figure 3B:
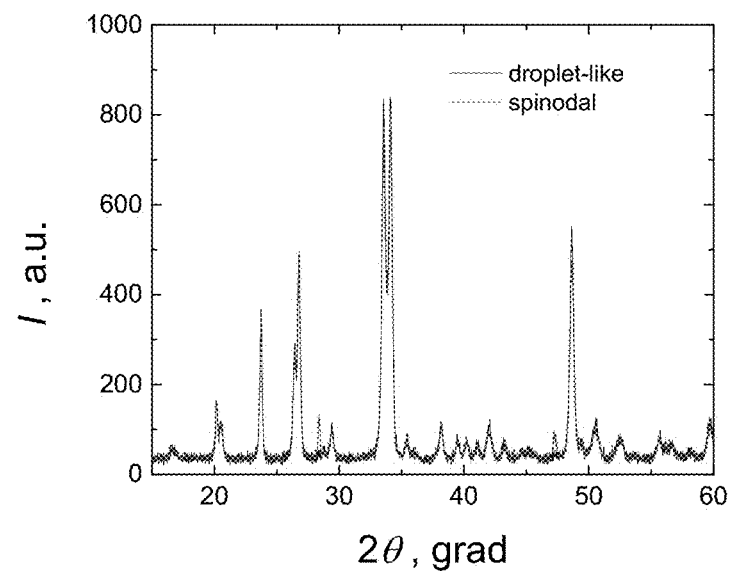
Figure 4A:
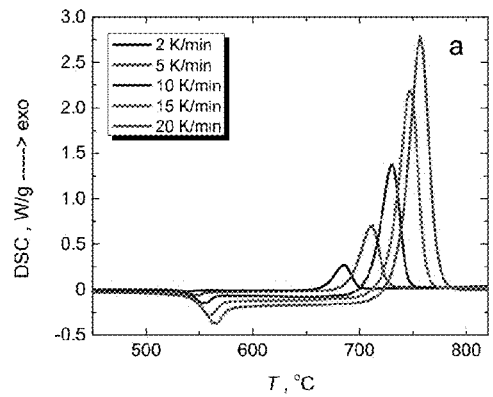
FIG. 4(a)-(d) show typical DSC heating curves for spinodally (a, b) and droplet-like (c, d) phase separated 45S5 glasses measured for the bulk (a, c) and <32 μm powder (b, d) samples.
Figure 4B:
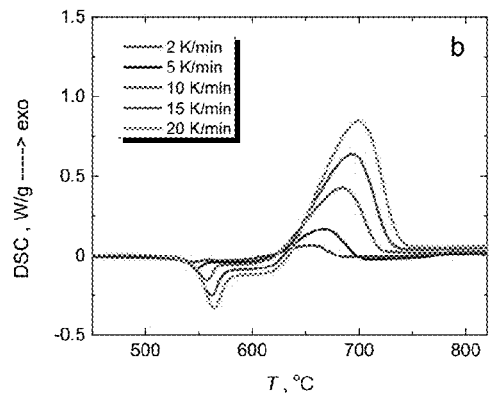
Figure 4C:
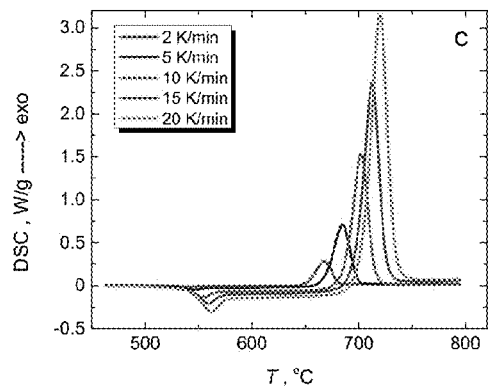
Figure 4D:
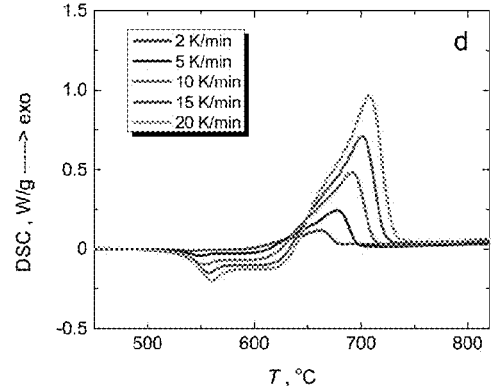

The 45S5 glass transforms into a glass-ceramic by heating the material at >700° C. for more than 0.5 h, resulting in several possible crystalline phases viz. $Na_2Ca_2Si_3O_9$, $Na_2CaSi_2O_6$-combeite and $Na_2Ca_4(PO_4)_2SiO_4$-silicorhenanite. XRD data of as-prepared glasses and fully crystallized samples (after DSC scans) are shown in FIG. 3. Predominant crystalline phase identified in both ceramics prepared from droplet-like and spinodally phase-separated parent glasses is combeite $Na_2CaSi_2O_6$. For a spinodally phase-separated glass the additional reflections in FIG. 3b are caused by crystalline Si, which was added to the powder for calibration purposes.

Figure 6:
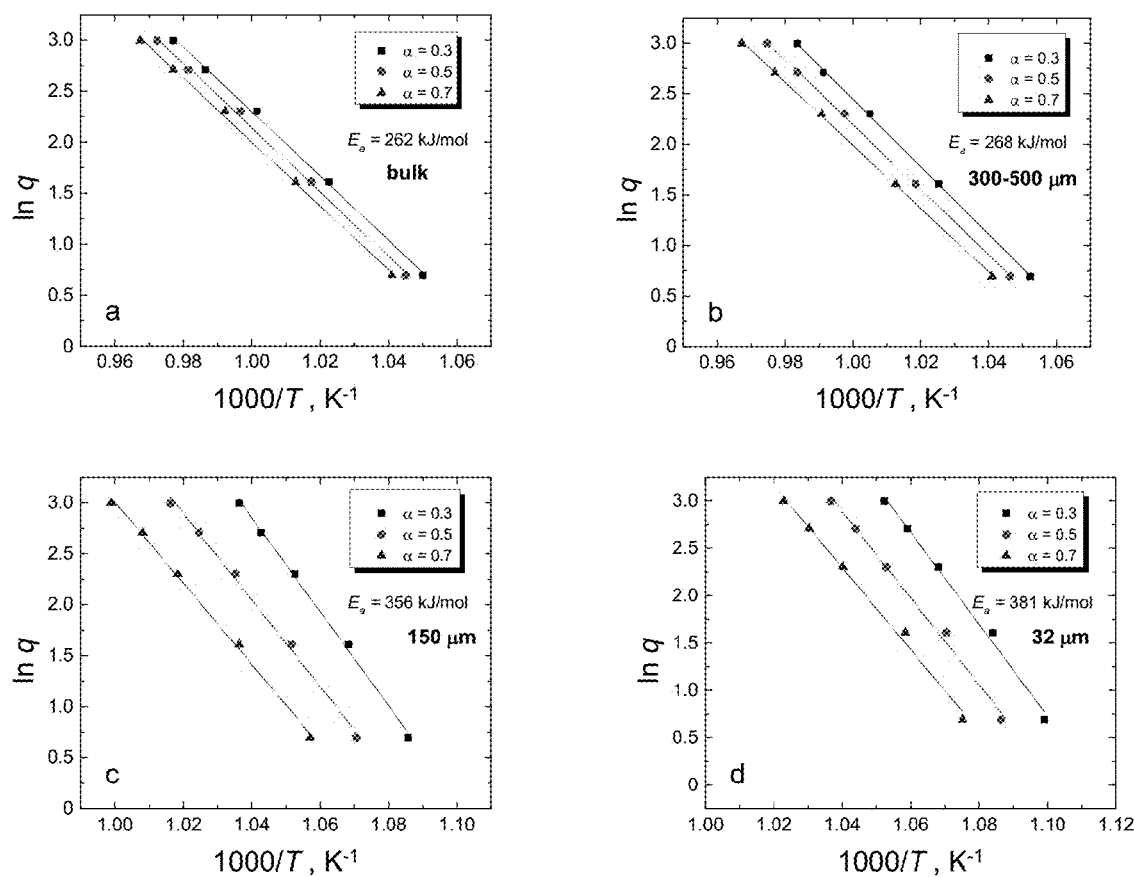
FIG. 6 shows Ozawa plots for the estimation of the crystallization activation energy for spinodally phase-separated glass of different particle size.
Figure 7:
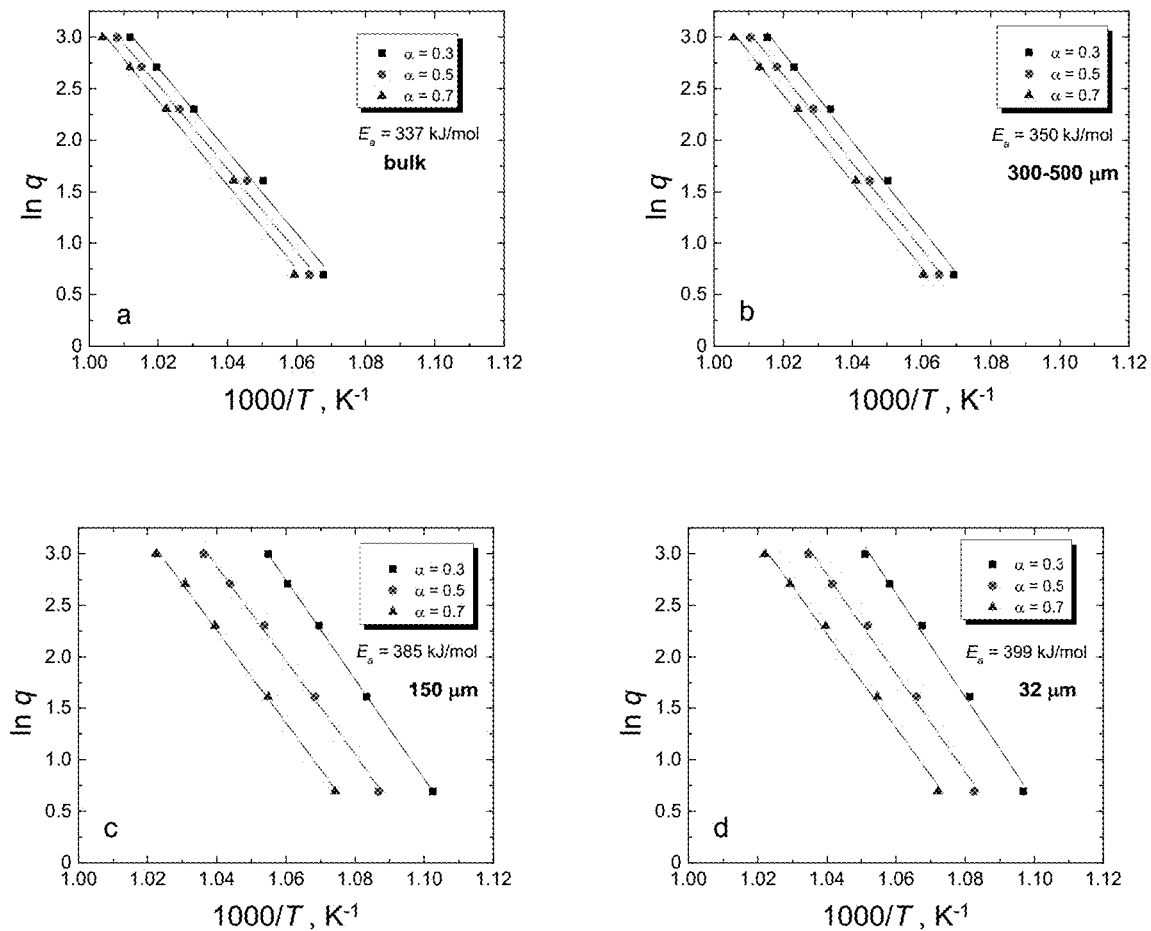
FIG. 7 shows Ozawa plots for the estimation of the crystallization activation energy for droplet-like phase-separated glass of different particle size.

From comparison of typical DSC scans for the investigated samples (FIGS. 4 and 5) it can be ascertained that crystallization kinetics differs for glasses with different types of phase separation and it also depends on whether the sample is in bulk or powder form. In particular, the activation energy of crystallization calculated according to the Ozawa method is found to be higher for the bulk glass with droplet-like phase separation (compare curves for bulk samples in FIGS. 6 and 7). This can be explained by the fact that crystallization of this glass starts at ~30 K lower temperatures than that of the spinodally phase separated sample, where the viscosity of supercooled liquid is generally higher. The higher viscosity means more constraints for structural rearrangements needed for crystallization to occur. In the case of glass with spinodal type of phase separation, crystallization starts at higher temperatures where the viscosity of the supercooled liquid is lower (FIGS. 6 and 7) and structural rearrangements are easier. Accordingly, Applicants have determined that that big droplets of Na/Ca/P-rich phase provide more nuclei for crystallization, initiating the process at lower temperatures.

Figure 5A:
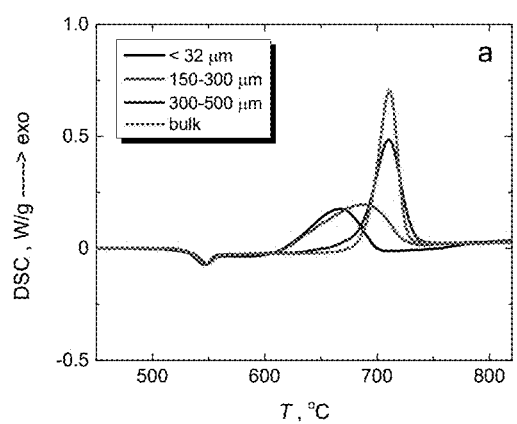
FIGS. 5(a) and (b) show DSC heating curves for spinodally and droplet-like phase separated 45S5 glasses, respectively, measured for different particle size at 5 K/min heating rate.
Figure 5B:
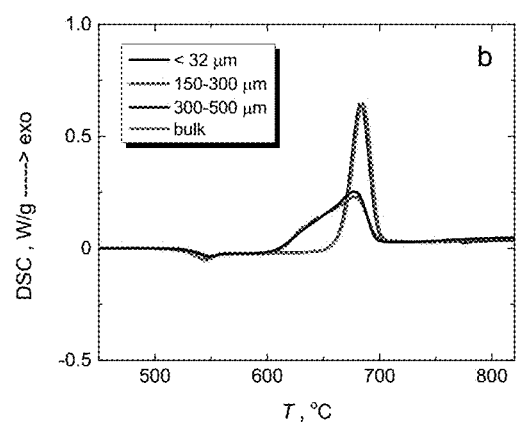

Decrease in the particle size of powder samples causes significant broadening of the crystallization peak and its shift towards lower temperatures (see e.g., FIGS. 4 and 5). The activation energy for crystallization becomes much higher than for the bulk samples and almost equal in magnitude for the droplet-like and spinodally phase-separated glasses when the particle size is less than 150 μm (see e.g. FIGS. 6 and 7). The onset temperature of crystallization also becomes almost the same for both types of the material and simultaneously shifts by ~30-50 K towards lower values in comparison to bulk crystallization. Therefore, Applicants have determined that extended surface area of powdered samples provides a high enough concentration of nucleation sites that the entire crystallization is governed by the processes on the surface.

Figure 8:
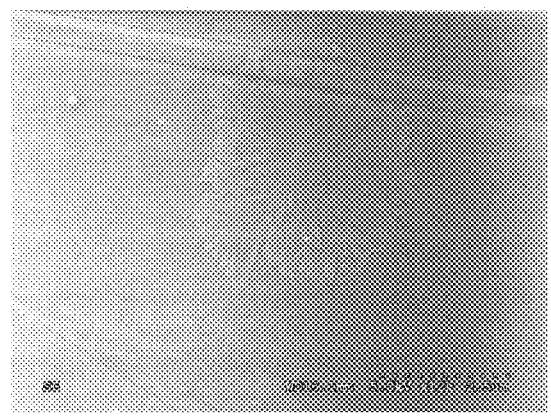
FIG. 8 shows a typical polycrystal formed at the surface of 45S5 sample.

A typical SEM picture of polycrystal formed at the surface of 45S5 BG is shown in FIG. 8. The value of the crystallization activation energy for powdered samples of <300 μm sizes (~350-390 kJ/mol) agrees well with activation energy values ~350 kJ/mol obtained earlier for 45S5 powder prepared by tape casting technique (particle sizes <10 μm).

The crystallization kinetics as studied with DSC are usually analyzed with Johnson-Mehl-Avrami (JMA) nucleation-growth model. However, the JMA equation for non-isothermal conditions is valid only if a certain number of criteria are satisfied: the entire nucleation process takes place during the early stages of the transformation, and becomes negligible afterward; the overall crystallization rate is defined only by the temperature and does not depend on the previous thermal history. Fundamental kinetic equations for non-isothermal crystal growth from preexisting nuclei have been developed by Ozawa and a simple method of kinetic analysis of DSC data for these processes has been proposed:

$$\frac{d\alpha}{dt} = Af(\alpha)e^{\left(-\frac{E_a}{RT}\right)} \quad (1)$$

where α is fraction of crystallized volume $$\alpha = \frac{1}{\Delta H_c} \int_0^T \phi dT. \quad (2)$$

Here φ is the specific heat flow measured with DSC (W/g) and $\Delta H_c$ is the total enthalpy change associated with the crystallization process; the pre-exponential factor A and activation energy $E_a$ are kinetic parameters that should not depend on the temperature T and α; and $$f(\alpha) = m(1-\alpha)[-\ln(1-\alpha)]^{1-1/m} \quad (3)$$

is an algebraic expression of the JMA model.

It has been demonstrated that the JMA exponent m is a characteristic parameter linked to crystal forming morphology. In particular, m~1 means predominant surface crystallization, while m~3 corresponds to three-dimensional bulk crystallization. If one applies JMA model straight to the investigated 45S5 glasses, then m≈1 is typically obtained for powdered samples with <300 μm particle sizes and m≈3-4 for the bulk samples. However, the validity of JMA equation for the investigated glasses should be demonstrated first. A simple test for the applicability of JMA model is proposed by Malek. It is based on the analysis of probe functions:

$$y(\alpha) = \phi e^{\left(-\frac{E_a}{RT}\right)} \quad (4)$$

$$z(\alpha) = \phi T^2 \quad (5)$$

Figure 9A:
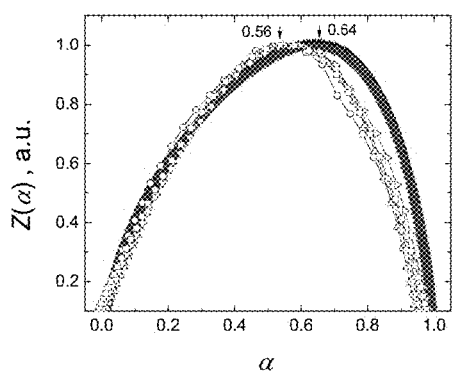
FIGS. 9(a) and (b) show $Z(\alpha)$ functions for spinodally and droplet-like phase separated 45S5 glasses, respectively, wherein open symbols correspond to bulk samples, full symbols stand for <32 μm size powder.
Figure 9B:
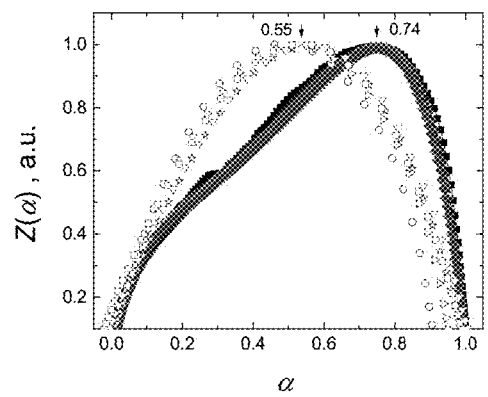

For JMA equation to be valid the maximum of the z(α) function should occur around α=0.63±0.02 value. As seen from FIG. 9, the maximum for z(α) function is around α=0.55-0.56 for bulk (and powder with particle sizes >300 μm) samples of both spinodally and droplet-like phase-separated samples. Accordingly, we may conclude that the JMA equation is not applicable to describe the crystallization kinetics of bulk 45S5 BG, which is consistent with previous studies. The same is true for powdered samples with particle sizes <300 μm of droplet-like phase separated glass, which also demonstrate significant deviation from α=0.63 value expected for the validity of the JMA model (FIG. 9b); the α values are significantly higher than predicted. However, in the case of spinodally phase-separated glass (FIG. 9a), the JMA model can be applied for the analysis of crystallization kinetics of powder samples with small particle sizes (<300 μm). Accordingly, the mean value of m (about 1) obtained for small particles (<300 μm) of spinodally phase-separated glass is consistent with surface initiated crystallization mechanism proposed by Clupper and Hench for tape cast 45S5 glass (particle size less than 10 μm). Therefore, Applicants have determined that for small particle sizes (when the crystallization is mostly surface-driven) and spinodal-like phase separation, the crystallization kinetics can still be approximated with the JMA model.

The evolution of nanopores during phase separation and crystallization is studied with PAL spectroscopy. The main potential of the PAL spectroscopy method lies in its ability to characterize the local free volumes (including both open and closed pores) in materials on a sub-nanometer scale. The PAL method is particularly effective when positronium (Ps) is formed (ortho-Ps and para-Ps), because the energetic and geometric characteristics of this electron-positron bound state (hydrogen-like atom) are well determined, which allow quantification of free volume dimensions. Thus, it is possible to estimate the average hole size from the ortho-Ps lifetime in a given material. Assuming approximately spherical shape of the free volume, the ortho-Ps lifetime ($\tau_o$) can be related to the average radius of holes (R) by a semi-empirical Tao-Eldrup equation:

$$\tau_o = \left[2\left(1 - \frac{R}{R+\Delta R} + \frac{1}{2\pi}\sin\left(\frac{2\pi R}{R+\Delta R}\right)\right) + 0.007\right]^{-1}, \quad (6)$$

where $\Delta R$ is an empirically determined parameter (in the classical case $\Delta R \approx 0.1656$ nm), describing effective thickness of the electron layer responsible for the pick-off annihilation of ortho-Ps in the hole.

Figure 10A:
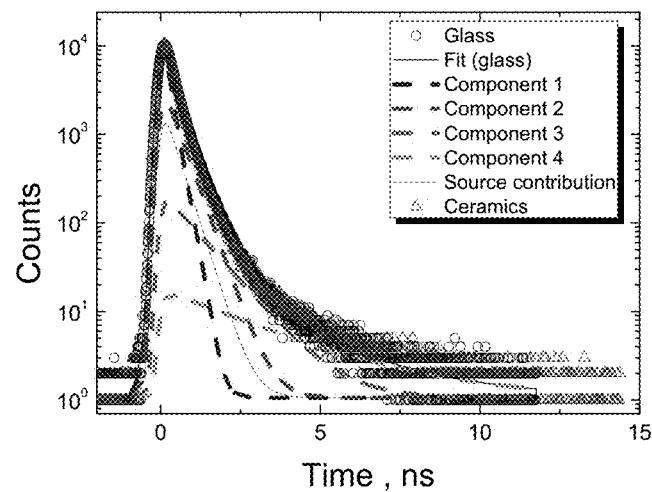
FIGS. 10(a) and (b) show positron annihilation lifetime (PAL) spectra obtained for spinodally and droplet-like phase-separated 45S5 glasses and ceramics, respectively, with example of fitting components for glass samples.
Figure 10B:
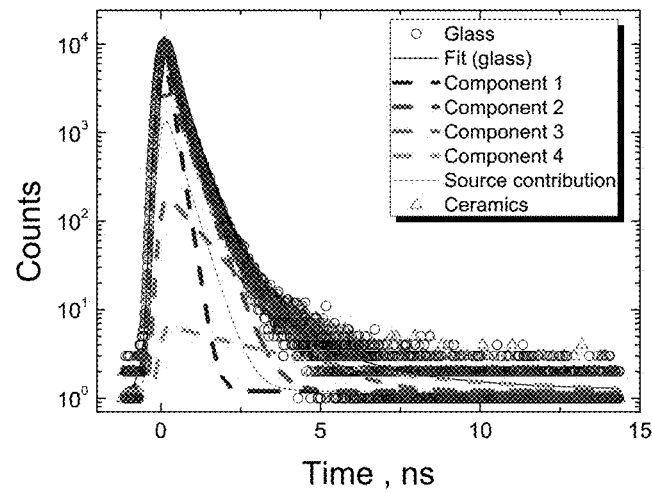

Typical PAL spectra for 45S5 glasses and glass-ceramics are shown in FIG. 10, giving the best-fit parameters as listed in Table 2. Four discrete exponentially decaying components can be distinguished in these spectra (FIG. 10), using iterative curve fitting procedure of the LT program. The first component ($\tau_1$, $I_1$) includes free annihilation, para-Ps decay and is related also to the positrons' bulk lifetime ($\tau_b$) in the sample. The second component ($\tau_2$, $I_2$) is usually caused by positrons that are trapped before annihilation in the free volume devoid of significant electron density in the glass structure, where formation of Ps is impossible for any other reason (geometric, energetic, inhibition of Ps formation, etc.). However, this component may convolute with greater bulk lifetime component of another phase, if it is present in the material.

The remaining two components ($\tau_3$, $I_3$), ($\tau_4$, $I_4$) can be directly associated with ortho-Ps formation (Table 2). These lifetimes can be related to corresponding pores via Tao-Eldrup relation (Eq. (6)) assuming ortho-Ps is in the ground (often denoted as "1 s") state, which is usually satisfied at low temperatures and for relatively small pores. As seen from Table 2, the as-prepared 45S5 glasses both spinodally and droplet-like phase-separated contain almost the same amount of voids $R_3 \sim 1.7$ Å in radius (estimated from $\tau_3$ and $I_3$ values). However, spinodally phase-separated glass contains more voids of larger radius $R_4 \sim 3.6$ Å (Table 2) in comparison to the droplet-like phase-separated material (estimated by $\tau_4$ and $I_4$ values).

TABLE 2

Fitting results of PAL measurements in phase separated 45S5 bioglass and derived ceramics: $\tau_i$ in ns, $I_i$ in % $R_i$ in Å.

| Sample | Component fit | | | | | | | | Voids | |
|---|---|---|---|---|---|---|---|---|---|---|
| | $\tau_1$ (0.005) | $I_1$ (1) | $\tau_2$ (0.005) | $I_2$ (1) | $\tau_3$ (0.01) | $I_3$ (0.4) | $\tau_4$ (0.05) | $I_4$ (0.2) | $R_3$ | $R_4$ |
| Spinodally phase separated | | | | | | | | | | |
| Glass | 0.180 | 50 | 0.420 | 44 | 1.026 | 4.7 | 2.859 | 1.0 | 1.73 | 3.58 |
| Ceramics | 0.180 | 55 | 0.420 | 41 | 1.467 | 2.8 | 3.762 | 0.6 | 2.33 | 4.16 |
| Droplet-like phase separated | | | | | | | | | | |
| Glass | 0.180 | 47 | 0.420 | 47 | 1.035 | 4.7 | 3.444 | 0.3 | 1.73 | 3.97 |
| Ceramics | 0.180 | 52 | 0.420 | 45 | 1.383 | 2.9 | 4.240 | 0.3 | 2.22 | 4.43 |

These void sizes normally are associated with fine pores within the oxide building blocks (individual coordination polyhedra) of the silica network and their interconnection. After droplet-like phase separation or ceramization process the voids agglomerate together, forming voids of larger dimensions ($R_3 \sim 3.2$-$3.3$ Å and $R_4 \sim 4.2$-$4.4$ Å in radii, see Table 2), which most probably reside within the boundaries between the devitrified crystallites and residual glassy phase, or different glassy phases. At the same time structure densifies at a finer scale, as indicated by the increase of $I_1$ intensity after ceramization of both types of 45S5 phase-separated parent glasses (Table 2). This behavior can be understood if one takes into account the fact that bulk lifetime of positrons is generally lower in crystalline material (formed crystallites) than in the corresponding glass.

The example shows that type of phase separation (spinodal vs. droplet-like) has a pronounced effect on the devitrification characteristics of 45S5 BG. In particular, it appears that activation energy of viscous flow for a spinodally phase separated 45S5 glass is lower than that for the droplet-like phase separated glass. Crystallization starts at lower temperatures and the activation energy of crystallization is higher for droplet-like phase separated glass, whereas the spinodally phase separated glass crystallizes at higher temperatures and, therefore, has a lower activation energy of crystallization. The JMA equation is found to be not applicable to the crystallization kinetics analysis for both types of bulk 45S5 BGs. However, for small particle sizes (<300 µm), where crystallization processes are mostly surface driven, JMA equation still works under certain conditions, viz. for spinodally phase separated 45S5 glass powder with small particle size. The nature of phase separation also affects the pore distribution at the nanoscale as shown by PAL spectroscopy. As-prepared 45S5 glasses both spinodally and droplet-like phase-separated contain almost the same amount of fine voids $R_3 \sim 1.7$ Å in radius, whereas spinodally phase-separated glass contains more voids of larger dimensions $R_4 \sim 3.6$ Å. This difference in sub-nanoscale structure is another possible mechanism for the difference in how the proteins and cells respond to them. After devitrification these voids show the tendency to agglomeration in both types of materials.

EXAMPLE 2

The following example demonstrates the bioactivity of a glass composition having a spinodal distribution. In this example, 45S5 bioglass is used which is characterized by its complex composition as follows:

24.4 mol % $Na_2O$ (sodium oxide)
26.9 mol % CaO (calcium oxide)
2.6 mol % $P_2O_5$ (phosphorus pentoxide)
46.1 mol % $SiO_2$ (silicon dioxide).

Figure 12A:
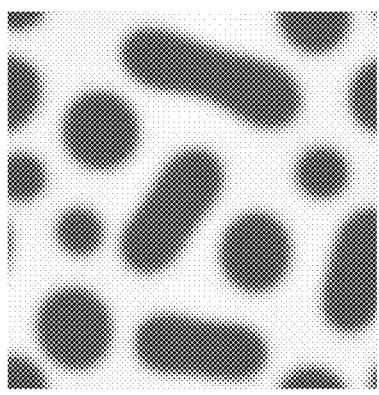
FIGS. 12(a) and (b) illustrate droplet and spinodal nanostructures, respectively, formed by quenching from varying temperatures.
Figure 12B:
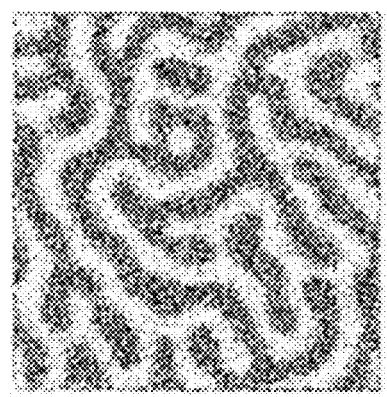

Referring to FIGS. 11 and 12, quenching from varying temperatures can alter 45S5 bioglass nanostructure as described above. Specifically, the melt-quench process is characterized by melting precursors at high temperatures followed by quenching (rapid cooling) the melt to room temperature, producing solid bioglass.

Figure 13A:
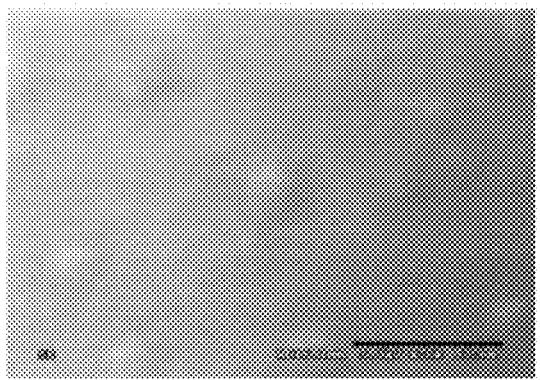
FIGS. 13(a) and (b) are SEM photos showing droplet and spinodal nanostructures, respectively.
Figure 13B:
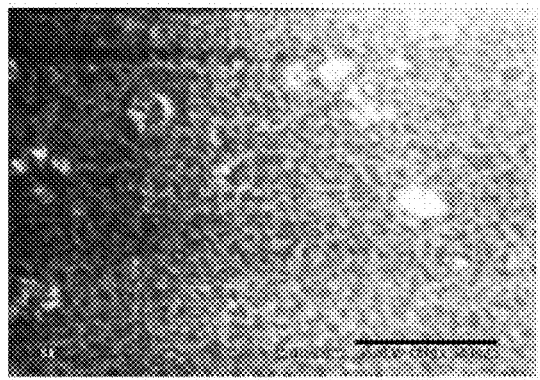

Here, three glass "batches" were rapidly cooled from 1550, 1380, and 1370° C. to room temperature. As discussed above, cooling the batches at these different temperatures resulted in different phase separation. The differences in phase separation result in varying nanostructure in, either isolated droplets (1370° C.) or spinodal interconnected (1380 & 1550° C.) morphology according to SEM observations. Specifically, referring to FIG. 13, nanostructure of 45S5 glass quench at 1370° C. with droplet (a), and at 1380 & 1550° C. with spinodal nanostructures (b) observed by SEM (scale bar: 500 nm).

Each cylindrical glass column produced from the three different samples was cut into a set of 2mm discs, polished to achieve an optical finish. All samples were re-cut, autoclaved, and sterilized through acetone washes. All samples were pre-incubated in PBS for 72 hrs at 37° C. All samples were seeded with 30,000 cells/$cm^2$ in 3.5 cm dishes and two samples from each batch were incubated for 2, 6, 12, and 24 hrs. Samples were then subsequently fixed, and stained for DAPI, A488-Phalloidin, and Vinculin. All samples were then imaged for cell density, morphology, and attachment.

It should be understood that, according to current research, upon contact with protein-rich body fluids, the surfaces of 45S5 bioglass samples are instantaneously coated and saturated with numerous extra-cellular matric (ECM) proteins, The cells of the body, therefore, do not actually contact the biomaterial itself, but rather attach to the molecular architecture of the surface-adsorbed proteins.

Referring to FIG. 14, the effects of nanostructure on cellular density and adhesion are shown. Specifically, in (i) and (ii), cell density was visualized with DAPI for the 1370° C. and 1550° C. samples, respectively, and, in (iii) and (iv), Actin was visualized with Alexa-488-Phalloidin for the 1370° C. and 1550° C. samples, respectively. MC3T3-E1 pre-osteoblasts fixed and imaged 2 hours after seeding onto 45S5 bioactive glass samples that were prepared by quenching the melt at 1370 and 1550° C. Note significant increase in cell number and attachment on the sample quenched at 1550° C.

Figure 15I:
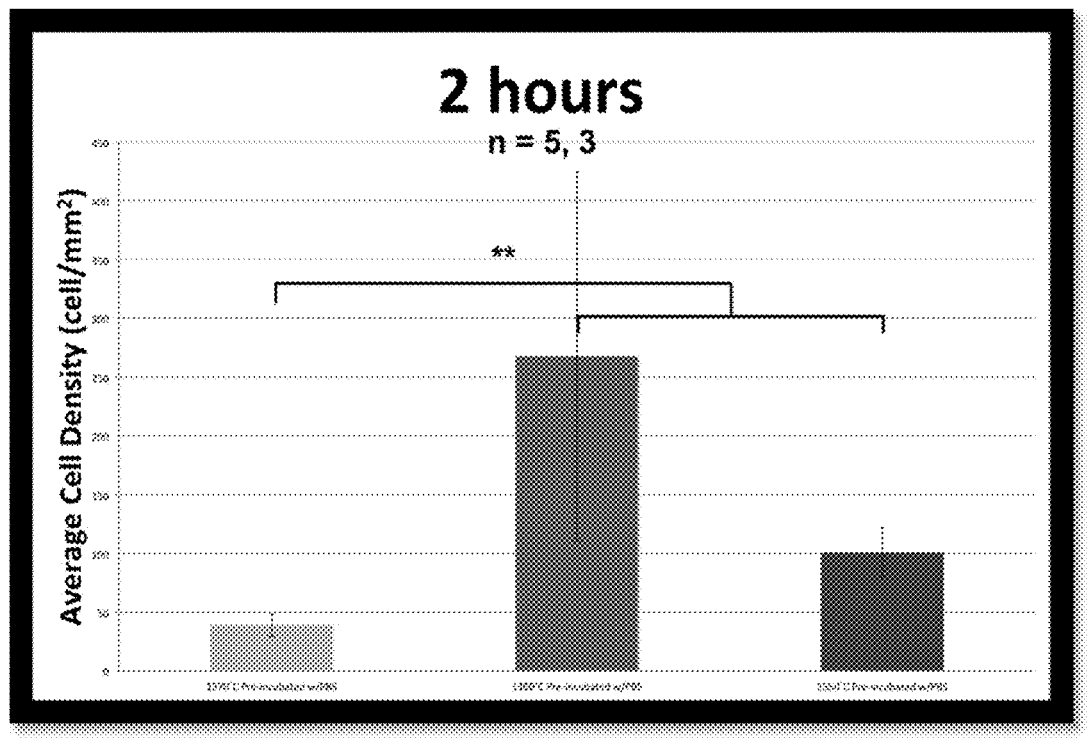
FIGS. 15(i)-(iv) shows results confirming that cells respond to differences in the nanostructure of 45S5 bioglass.
Figure 15:
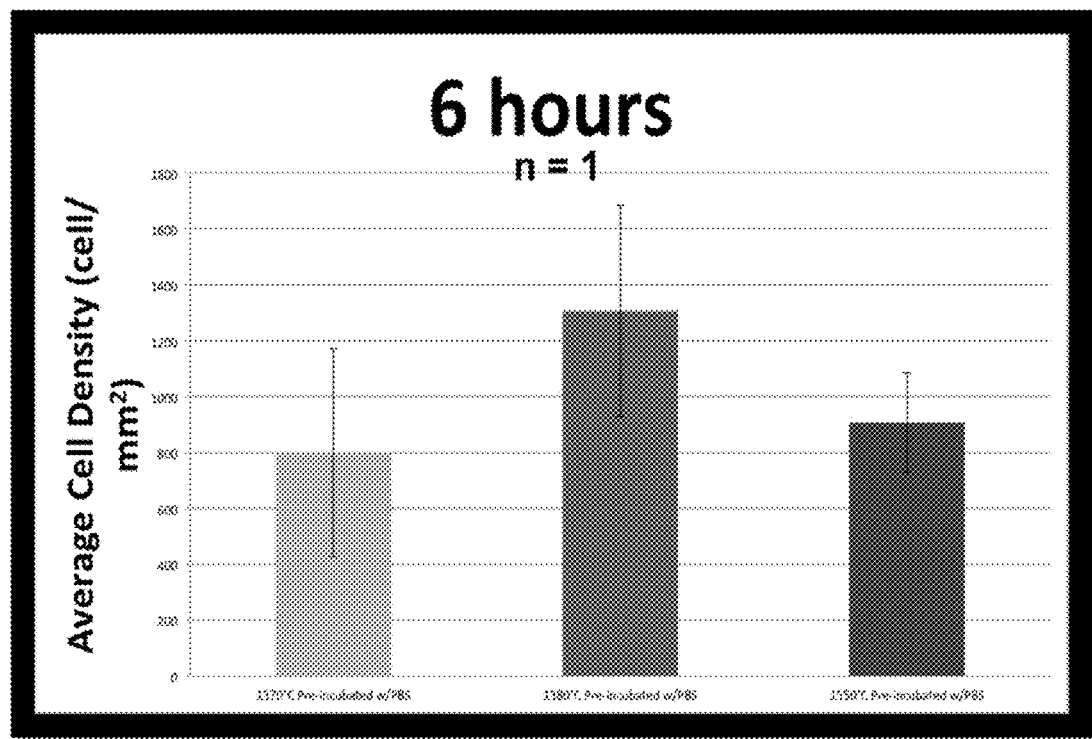
Figure 15:
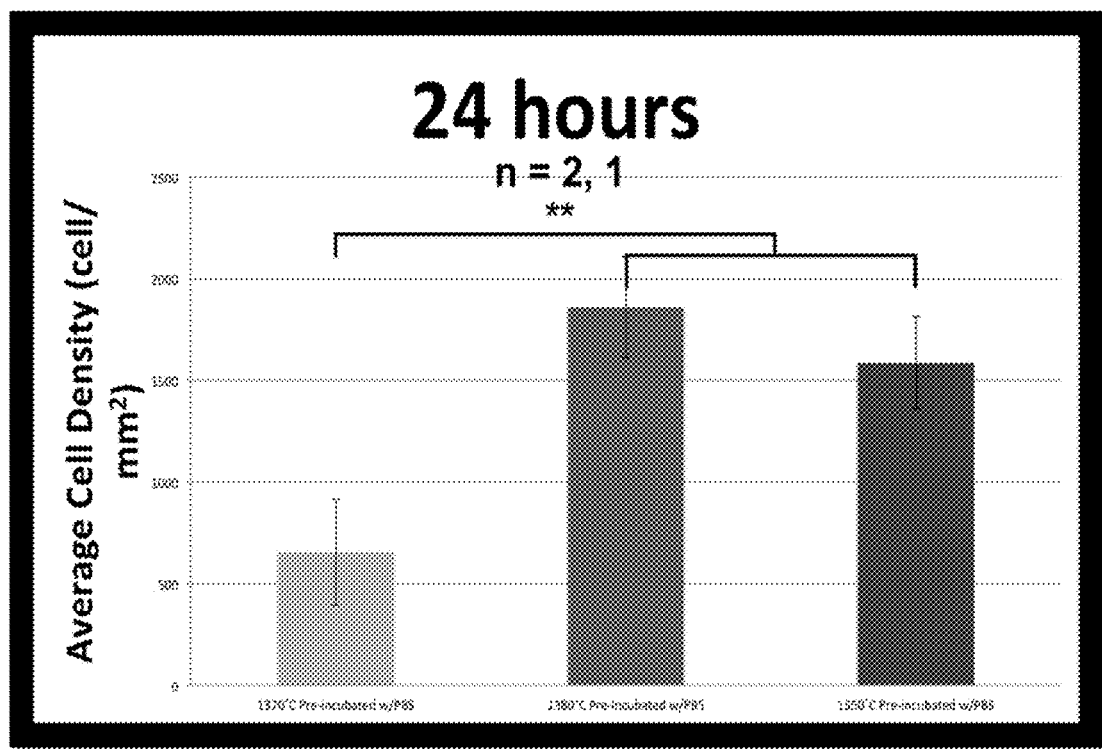

Referring to FIG. 15, results confirm that cells are able to respond to differences in the nanostructure of 45S5 bioglass. Average cell density of MC3T3-E1 preosteoblasts on polished 45S5 bioglass samples prepared by quenching the melt at 1370° C., 1380° C., and 1550° C. are shown. From the results above, it is evident that cells preferred 45S5 bioglass samples exhibiting spinodal nanostructure over the samples exhibiting droplet nanostructure. (i) 2H: We observed statistically significant differences between the 1370° C. and 1380° C. samples in five experiments, while statistically significant differences between 1370° C. & 1550° C. samples were observed in 3 experiments; (ii & iii) 6H & 12H: Statistically significant differences between the 1370° C. & 1380° C. samples and between 1370° C. & 1550° C. samples were observed once; (iv) 24H: Statistically significant differences between the 1370° C. & 1380° C. samples in 2 experiments were observed, while statistically significant differences between 1370° C. & 1550° C. samples were observed in 1 experiment.

Based on these results, a strong cellular preference for samples exhibiting spinodal nanostructure was observed. Specifically, the results show that cells are able to react to subtle architectural variations in 45S5 bioglass as cells attached to samples exhibiting spinodal nanostructure in larger numbers, consistently.

In conclusion, Applicants have discovered that a glass comprising spinodal type nanostructure is biomedically superior to the same glass comprising droplet type nanostructure. These two types of nanostructures can be obtained by controlling the melt cooling process, which may include the melt temperature, mold temperature, casting procedure, batch size, subsequent heat treatment, etc., among other process parameters that affect thermal history during glass formation. Applicants note that within the broad classification of spinodal or droplet type nanostructures, significant variations of the distribution of two phases exist, which also impact cell response. In other words, the conditions of glass fabrication may be further optimized for improving the cell response, but the basic premise of superior performance of the spinodal nanostructure will remain.

What is claimed is:

1. A method of using a glass to promote bioactivity, said method comprising:
    disposing said glass composition in a cellular environment, said glass having spinodal separation and being essentially free of pores; and
    facilitating cellular attachment and proliferation on said glass composition.

2. The method of claim 1, wherein said cellular attachment and/or proliferation is greater than that on glass having formed from the same mixture but with droplet phase separation or no phase separation.

3. The method of claim 1, wherein said cellular environment is a body of an animal.

4. The method of claim 3, wherein said cellular environment is a human body.

5. The method of claim 3, wherein facilitating cellular attachment comprises maintaining the life of the cells of said animal for an extended period of time.

6. The method of claim 5, wherein said animal is a human.

* * * * *